(12) United States Patent
Bold et al.

(10) Patent No.: US 7,790,888 B2
(45) Date of Patent: Sep. 7, 2010

(54) METHOD FOR PRODUCING TRIS-ORTHO-METALLATED COMPLEXES AND USE OF SUCH COMPLEXES IN OLEDS

(75) Inventors: Markus Bold, Dirmstein (DE); Peter Erk, Frankenthal (DE); Mairi Haddow, Blairgowrie (GB); Ingolf Hennig, Neulussheim (DE); Hans-Werner Schmidt, Bayreuth (DE); Markus Baete, Kulmain (DE); Mukundan Thelakkat, Bayreuth (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1339 days.

(21) Appl. No.: 10/555,595

(22) PCT Filed: Apr. 30, 2004

(86) PCT No.: PCT/EP2004/004610

§ 371 (c)(1),
(2), (4) Date: Nov. 7, 2005

(87) PCT Pub. No.: WO2004/099223

PCT Pub. Date: Nov. 18, 2004

(65) Prior Publication Data

US 2007/0080342 A1    Apr. 12, 2007

(30) Foreign Application Priority Data

May 5, 2003    (DE) ................................ 103 20 103

(51) Int. Cl.
*C07F 15/00* (2006.01)
(52) U.S. Cl. .............................. 546/2; 548/102; 313/504
(58) Field of Classification Search .................... 546/2; 548/102; 313/504
See application file for complete search history.

(56) References Cited

U.S. PATENT DOCUMENTS

2003/0068526 A1    4/2003    Kamatani et al. ........... 428/690

FOREIGN PATENT DOCUMENTS

| DE | 101 04 426 | 8/2002 |
|---|---|---|
| EP | 1 191 612 | 3/2002 |
| EP | 1 239 526 | 9/2002 |
| WO | 02/2714 | 1/2002 |
| WO | 03/040256 | 5/2003 |
| WO | 03/103341 | 12/2003 |

OTHER PUBLICATIONS

Mirco G. Colombo, et al., "Facial tris cyclometalated $Rh^{3+}$ and $Ir^{3+}$ complexes: their synthesis, structure, and optical spectroscopic properties", Inorganic Chemistry, vol. 33, No. 3, pp. 545-550 1994.
S. Sprouse, et al., "Photophysical effects of metal-carbon σ bonds in ortho-metalated complexes of Ir(III) and Rh(III)", J. AM. CHEM. SOC., vol. 106, No. 22, pp. 6647-6653 1984.
R. J. Watts, et al., "A new synthetic route to the preparation of a series of strong photoreducing agents: fac tris-ortho-metalated complexes of iridium (III) with substituted 2-phenylpyridines", INORG. CHEM., vol. 30, No. 8, pp. 1685-1687 1991.
Akira Tsuboyama, et al., "Homoleptic cyclometalated iridium complexes with highly efficient red phosphorescence and application to organic light-emitting diode", J. AM. CHEM. SOC., vol. 125, No. 42, pp. 12971-12979 2003.
Ying-Ju, Su, et al, "Highly efficient red electrophosphorescent devices based on iridium isoquinoline complexes: remarkable external quantum efficiency over a wide range of current", Adv. Mater., vol. 15, No. 11, pp. 884-888 Jun. 5, 2003.
Vladimir V. Grushin, et al., "New, efficient electroluminescent materials based on organometallic Ir complexes", CHEM. COMMUN., pp. 1494-1495 2001.

*Primary Examiner*—Porfirio Nazario Gonzalez
(74) *Attorney, Agent, or Firm*—Oblon, Spivak, McClelland, Maier & Neustadt, L.L.P.

(57) ABSTRACT

Process for preparing tris-ortho-metallated iridium complexes of the formula (I)

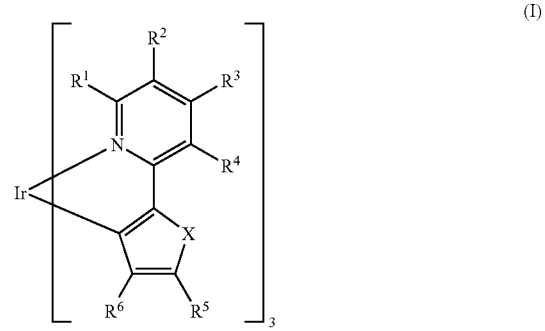

where $R^1$, $R^2$, $R^3$, $R^4$, $R^5$, $R^6$ and X have the meanings given in the description, Ir complexes which can be prepared by the process of the invention, the use of the Ir complexes as emitter molecule in organic light-emitting diodes (OLEDs), a light-emitting layer comprising the Ir complexes, an OLED comprising this light-emitting layer and an apparatus comprising an OLED according to the present invention.

10 Claims, 3 Drawing Sheets

METHOD FOR PRODUCING TRIS-ORTHO-METALLATED COMPLEXES AND USE OF SUCH COMPLEXES IN OLEDS

The present invention relates to a process for preparing tris-ortho-metallated iridium complexes, Ir complexes which can be prepared by the process of the present invention, the use of the Ir complexes as emitter molecule in organic light-emitting diodes (OLEDs), a light-emitting layer comprising the Ir complexes, an OLED comprising this light-emitting layer and an apparatus comprising an OLED according to the present invention.

The tris(phenylpyridine)iridium complex (Irppy$_3$) is one of the most important building blocks in the field of triplet emitters. In the prior art, the use of Irppy$_3$ in this field is described in numerous publications. An advantage of this class of compounds is that, in contrast to the customarily employed fluorescent dyes which in 75% populated triplet states can likewise be utilized in emission, they give a theoretical quantum yield of 100% provided that rapid intersystem crossing (ISC) occurs. R. J. Watts et al., J. Am. Chem. Soc. 1984, 106, 6647-6653, describe the first route to Irppy$_3$ by direct cyclometallation of IrCl$_3$x.3 H$_2$O by means of phenylpyridine. However, the desired Irppy$_3$ is obtained in a yield of only 10%, while the major part of the Ir complex obtained is made up by the dinuclear μ-chloro complex.

R. J. Watts et al., Inorg. Chem. 1991, 30, 1685-1687, relates to the preparation of Irppy$_3$ from the abovementioned μ-chloro complex by breaking up of the unit by means of 2,4-pentanedione and subsequent further (third) cyclometallation by means of phenylpyridine. Furthermore, the direct preparation of Irppy$_3$ from Ir(acac)$_3$ (acac=acetylacetonate) in glycerol at 200° C. is disclosed. A disadvantage is that this reaction gives a complex range of by-products which can be removed only with great difficulty, if at all, by customary purification operations (crystallization, chromatography, sublimation).

Bürgi et al., Inorg. Chem 1994, 33, 545-550, relates to the preparation of Irppy$_3$ from the μ-chloro complex by reaction with AgOTf (Tf=trifluoroacetate), so that a further reaction with phenylpyridine can be induced.

The formula of the abovementioned μ-chloro complex is:

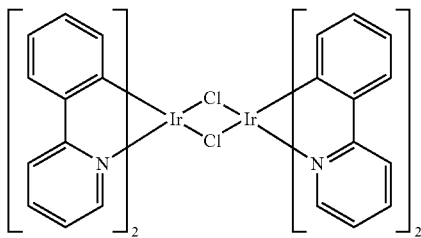

Apart from the Ir complex Irppy$_3$ which emits light in the green region of the electromagnetic spectrum, effective emitter molecules which emit light in the red region of the electromagnetic spectrum are of interest.

A. Tsuboyama et al. J. Am. Chem. Soc. 2003, 125, 12971-12979, disclose Ir(III) complexes of phenylisoquinoline which emit light in the red region of the electromagnetic spectrum. They are prepared from Ir(acac)$_3$ by reaction with phenylisoquinoline. The desired complex is obtained in a yield of 27%.

Su et al. Adv. Mater, 2003, 15, 884-888, relates to the preparation of substituted Ir-phenylisoquinoline complexes. These are prepared by means of a multistage reaction, in which a chloro-bridged Ir dimer is reacted with an excess of ligand in the presence of Ag(CF$_3$SO$_3$) to give the desired Ir complex.

EP-A 1 191 612 relates to light-emitting diodes comprising tris-ortho-metallated complexes of Ir, Rh or Pd. Among other compounds, Ir complexes of 2-benzo[b]thiophen-2-ylpyridine are disclosed. They are synthesized from Ir(acac)$_3$ by reaction with 2-benzo[b]thiophen-2-ylpyridine. The desired complex is obtained in a yield of 23%.

WO 03/103341 relates to OLEDs which comprise a phosphorous and light-emitting material in the light-emitting layer. The tris-ortho-metallated Ir complex of phenylisoquinoline is used as material which emits red light. A method of preparing the Ir complex is not indicated.

WO 03/040256 relates to Ir(III) complexes which emit red-orange or red light. Among other compounds, the tris-ortho-metallated Ir complex of deuterated phenylisoquinoline is disclosed. The complex is prepared via preparation of the μ-chloro complex. Furthermore, the Ir(III) complex bearing two phenylisoquinoline ligands and one acac ligand is disclosed.

EP-A 1 239 526 relates to metal complexes of the formula ML$_m$L'$_n$, where M can be, inter alia, Ir and L and L' are different bidentate ligands, with n being able to be 0 if appropriate. The complexes are prepared either via preparation of the μ-chloro complexes or from the corresponding acac complexes.

Vladimir V. Grushin et al., Chem. Commun., 2001, 1494-1495, relates to Ir(III) complexes comprising fluorinated phenylpyridines as ligands and their use in OLEDs. The Ir(III) complexes are prepared by reacting IrCl$_3$ with fluorinated 2-arylpyridines in the presence of AgO$_2$CCF$_3$. However, the device data of the OLEDs comprising the Ir(III) complexes mentioned are capable of improvement.

WO 02/02714 relates to electroluminescent Ir(III) complexes comprising fluorinated phenylpyridines, phenylpyrimidines or phenylquinolines as ligands, and to electronic devices whose active layer comprises an electroluminescent Ir(III) complex. The iridium(III) complexes with fluorinated phenylpyridines can be prepared by reacting the fluorinated phenylpyridines with IrCl$_3$ hydrate in the presence of Ag(OTf) in the absence of solvents.

DE-A 101 04 426 relates to a process for preparing highly pure, tris-ortho-metallated organoiridium compounds such as Ir(ppy)$_3$. The compounds mentioned can be prepared by reacting Ir(acac)$_3$ (acac=acetylacetonate) with appropriate organic ligands, in the case of Ir(ppy)$_3$ phenylpyridine, in a dipolar protic solvent or by reacting the appropriate organic ligands, in the case of Ir(ppy)$_3$ phenylpyridine; to form the corresponding lithium salt and subseqeuently reacting this with an Ir(III) compound, e.g. iridium(III) chloride, at low temperatures. The compounds are obtained in high purity form only after complicated HPLC.

Figure 1:
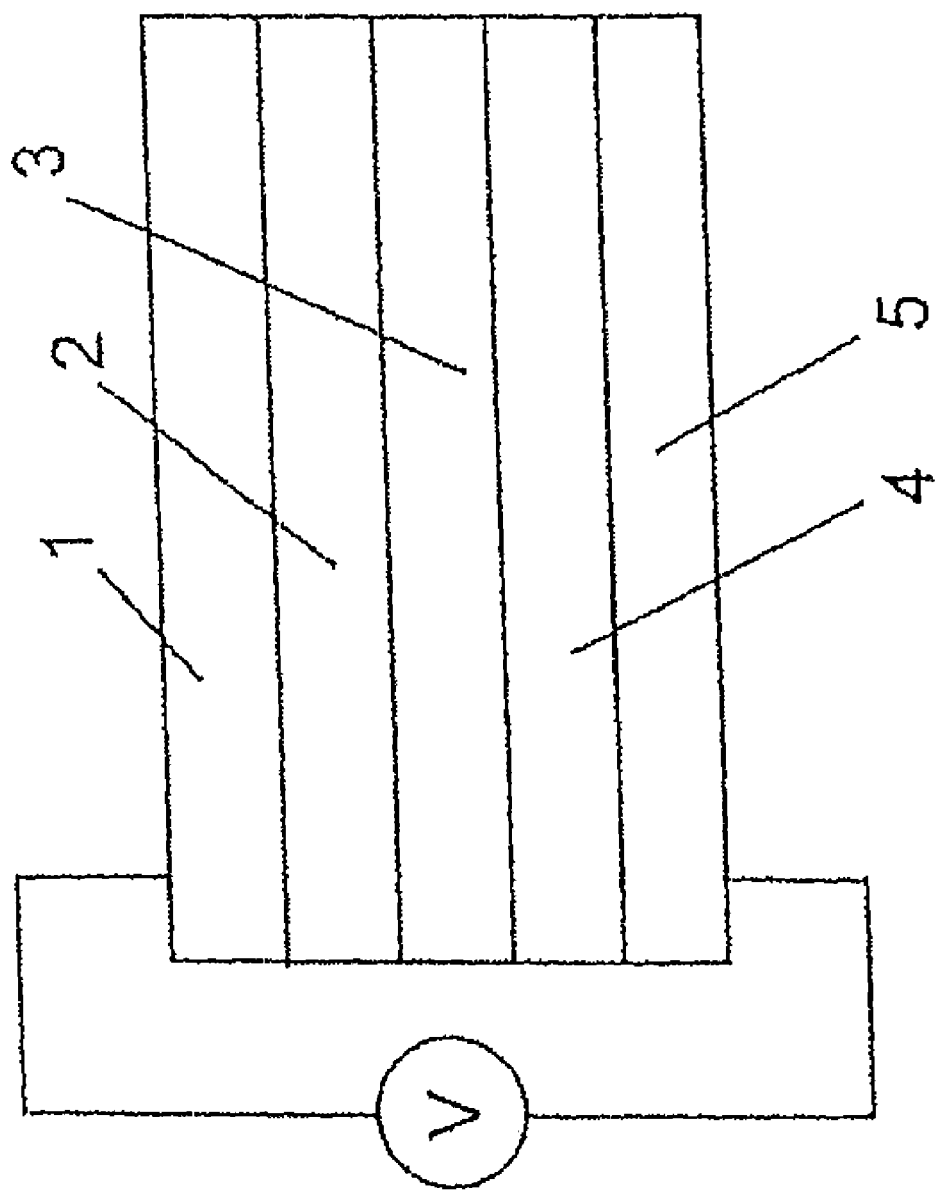
FIG. 1 shows the basic structure of Organic light-emitting diodes (OLEDs).

It is an object of the present invention to provide a process for preparing tris-ortho-metallated Ir complexes which is simple (one stage) and in which the highly pure Ir complexes can be prepared without complicated purification steps.

We have found that this object is achieved by a process for preparing compounds of the formula (I)

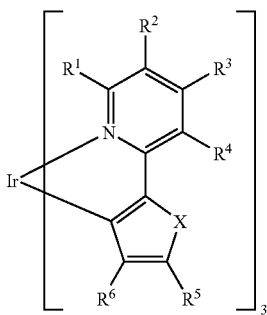

(I)

where
X is —CR$^7$=CR$^8$—, —S—, —NR$^9$—, —O—, —Se—;
R$^1$, R$^2$, R$^3$, R$^4$,
R$^5$, R$^6$, R$^7$ and
R$^8$ are each, independently of one another, H, straight-chain or branched C$_{1-20}$-alkyl, cyclic C$_{3-20}$-alkyl, where one or more nonadjacent CH$_2$ groups of the alkyl groups may be replaced by —O—, —S—, —NR$^{10}$— or —CONR$^{11}$— and one or more H atoms of the alkyl groups may be replaced by F, Cl, Br or CN; aryl or heteroaryl having a skeleton having from 4 to 14 carbon atoms, where one or more carbon atoms may be replaced by heteroatoms selected from among —O—, —S—, —N— and —P— and the carbon atoms and any heteroatoms may be substituted by nonaromatic substituents as defined for R$^1$ to R$^8$; F, Cl, Br or CN;
or
two adjacent radicals R$^1$, R$^2$, R$^3$, R$^4$, R$^5$, R$^6$, R$^7$ and R$^8$ together form a cyclic radical which may in turn be substitiuted by the groups mentioned for R$^1$, R$^2$, R$^3$, R$^4$, R$^5$, R$^6$, R$^7$ and R$^8$, where two adjacent substituents of the cyclic radical may in turn form a cyclic radical;
R$^9$, R$^{10}$,
R$^{11}$ are each, independently of one another, H, straight-chain or branched C$_{1-20}$-alkyl, cyclic C$_{3-20}$-alkyl which may be substituted as defined for the radicals R$^1$ to R$^8$, or aryl or heteroaryl is defined as for R$^1$ to R$^8$;

by reacting a ligand of the formula (II)

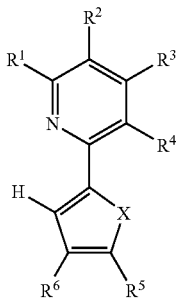

(II)

where the symbols R$^1$, R$^2$, R$^3$, R$^4$, R$^5$, R$^6$ and X are as defined above, with an iridium halide or pseudohalide of the formula IrZ$_3$ or IrZ$_3$.L$_x$, where Z is a halide or pseudohalide and L is an organic or inorganic molecule and x is the number of molecules L and is from 1 to 3, preferably 3; e.g. IrZ$_3$.L$_x$ can be

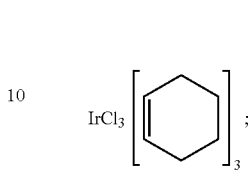

in the presence of a halide scavenger selected from the group consisting of Ag, Hg, Sb and Al salts.

X is preferably —CR$^7$=CR$^8$— or —S—, where R$^7$ and R$^8$ are each preferably, independently of one another, H, F or C$_{1-10}$-alkyl which may be straight-chain or branched, particularly preferably H or F. Particular preference is given to at least R$^7$ or R$^8$ being H and the further radical being H, F or C$_{1-10}$-alkyl which may be straight-chain or branched, preferably H or F. Very particular reference is given to R$^7$ or R$^8$ each being H. X is thus very particularly preferably —CH=CH— or —S—.

R$^1$, R$^2$, R$^3$, R$^4$, R$^5$ and R$^6$ are each preferably, independently of one another, H; straight-chain or branched C$_{1-10}$-alkyl, where one or more nonadjacent CH$_2$ groups of the alkyl groups may be replaced by —O— or —NR$^{10}$—, i.e. R$^1$ to R$^6$ can be alkoxy or amino radicals, and one or more H atoms of the alkyl groups may be replaced by F, Cl, Br or CN; aryl or heteroaryl having a skeleton having 5 or 6 carbon atoms, where one or more carbon atoms may be replaced by heteroatoms selected from among —O—, —S— and —N—;

or two adjacent radicals R$^1$ to R$^6$ together form a cyclic radical which may in turn be substituted by the groups mentioned for R$^1$ to R$^6$, preferably a 5- or 6-membered cyclic radical which may be saturated or unsaturated and may be substituted or unsubstituted, particularly preferably a 6-membered aromatic radical which is unsubstituted; very particular preference is given to R$^3$ and R$^4$ or R$^5$ and R$^6$ together forming a 6-membered aromatic radical which is unsubstituted and the further radicals not forming cyclic radicals.

R$^9$, R$^{10}$, R$^{11}$ are each preferably, independently of one another, H, straight-chain or branched C$_{1-10}$-alkyl or aryl or heteroaryl as defined for R$^1$ to R$^6$. Very particular preference is given to R$^9$, R$^{10}$, R$^{11}$ each being, independently of one another, H, C$_{1-3}$-alkyl or C$_6$-aryl which may optionally be substituted. Very particular preference is given to R$^9$, R$^{10}$, R$^{11}$ each being, independently of one another, H, methyl, ethyl or phenyl.

In a particularly preferred embodiment,
X is —CR$^7$=CR$^8$—, where R$^7$ and R$^8$ are each preferably, independently of one another, H, F or C$_{1-10}$-alkyl which may be straight-chain or branched, particularly preferably H or F, with very particular preference being given to at least R$^7$ or R$^8$ being H, in particular —CH=CH—, and
R$^1$, R$^2$,
R$^3$, R$^4$, $R^5$, $R^6$ are each, independently of one another, H, straight-chain or branched $C_{1-10}$-alkyl, where one or more nonadjacent $CH_2$ groups of the alkyl groups may be replaced by —O— or —$NR^{10}$—, i.e. $R^1$ to $R^6$ can be alkoxy or amino radicals, and one or more H atoms of the alkyl groups may be replaced by F, Cl, Br or CN; aryl or heteroaryl having a skeleton having 5 or 6 carbon atoms, where one or more carbon atoms may be replaced by heteroatoms selected from among —O—, —S— and —N—; with preference being given to $R^1$, $R^2$, $R^3$, $R^4$, $R^5$ and $R^6$ each being H.

In a further preferred embodiment,

X is —$CR^7$=$CR^8$—, where $R^7$ and $R^8$ are each preferably, independently of one another, H, F or $C_{1-10}$-alkyl which may be straight-chain or branched, particularly preferably H or F, with very particular preference being given to at least $R^7$ or $R^8$ being H, in particular —CH=CH—;

and $R^1$, $R^2$, $R^5$ and $R^6$ are each, independently of one another, H, straight-chain or branched $C_{1-10}$-alkyl, where one or more nonadjacent $CH_2$ groups of the alkyl groups may be replaced by —O— or —$NR^{10}$—, i.e. $R^1$, $R^2$, $R^5$ and $R^6$ can be alkoxy or amino radicals, and one or more H atoms of the alkyl groups can be replaced by F, Cl, Br or CN; aryl or heteroaryl having a skeleton having 5 or 6 carbon atoms, where one or more carbon atoms may be replaced by heteroatoms selected from among —O—, —S— and —N—; with preference being given to $R^1$, $R^2$, $R^5$ and $R^6$ each being H;

and $R^3$ and $R^4$ together form a cyclic radical which may in turn be substituted by the groups mentioned for $R^1$, $R^2$, $R^5$ and $R^6$, preferably a 5- or 6-membered cyclic radical which may be saturated or unsaturated and may be substituted or unsubstituted, particularly preferably a 6-membered aromatic radical which is unsubstituted.

In a further preferred embodiment,

X is —S—, and $R^1$, $R^2$, $R^3$ and $R^4$ are each, independently of one another, H, straight-chain or branched $C_{1-10}$-alkyl, where one or more nonadjacent $CH_2$ groups of the alkyl groups may be replaced by —O— or —$NR^{10}$—, i.e. $R^1$, $R^2$, $R^3$ and $R^4$ can be alkoxy or amino radicals, and one or more H atoms of the alkyl groups may be replaced by F, Cl, Br or CN; aryl or heteroaryl having a skeleton having 5 or 6 carbon atoms, where one or more carbon atoms may be replaced by heteroatoms selected from among —O—, —S— and —N—; with preference being given to $R^1$, $R^2$, $R^3$ and $R^4$ each being H;

and $R^5$, $R^6$ together form a cyclic radical which may in turn be substituted by the groups mentioned for $R^1$, $R^2$, $R^3$ and $R^4$, preferably a 5- or 6-membered cyclic radical which may be saturated or unsaturated and may be substituted or unsubstituted, particularly preferably a 6-membered aromatic radical which is unsubstituted.

The present invention very particularly preferably provides a process for preparing Ir complexes having the following formulae Ia, Ib and Ic:

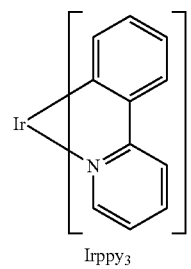

Irppy$_3$

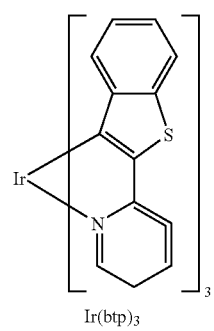

Ir(btp)$_3$

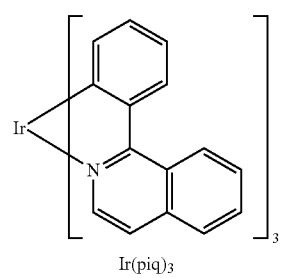

Ir(piq)$_3$ by reaction of the corresponding ligands of the formulae IIa, IIb and IIc:

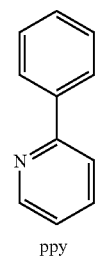

ppy

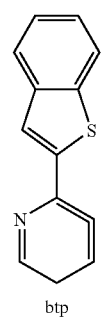

btp

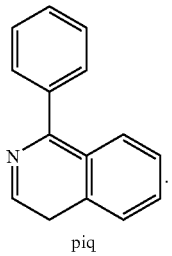

piq

The process of the invention for preparing a compound of the formula I is carried out by reacting a compound of the formula II with an iridium halide or pseudohalide of the formula $IrZ_3$ or $IrZ_3 \times L_x$, where Z is a halide, preferably Br or Cl, particularly preferably Cl, or a pseudohalide, preferably a cyanide, cyanate or thiocyanate, and L is an organic or inorganic molecule comprising a donor atom, e.g. tetrahydrofuran, pyridine, tetrahydrothiophene or water. x is preferably from 1 to 3.

The reaction is carried out in the presence of a halide scavenger which is selected from the group consisting of Ag, Hg, Sb and Al salts.

For the present purposes a halide scavenger or pseudohalide scavenger is a compound (generally a salt) which forms a sparingly soluble salt with halide ions or pseudohalide ions.

Preferred halide scavengers are Ag(I) salts. Suitable Ag(I) salts are, for example, selected from among inorganic salts such as $AgNO_3$, $Ag_2CO_3$, $Ag_2SO_4$, $AgClO_4$ and organic salts such as Ag(OAc), Ag(OTf). Ag(OTf) is very particularly preferred.

The process of the present invention is carried out in a solvent from the group consisting of aromatic solvents and amphoteric solvents such as alcohols having generally from 1 to 10 carbon atoms, preferably from 1 to 6 carbon atoms, or alkoxy alcohols such as ethoxyethanol or aryloxy alcohols. The solvents preferably have a boiling point of $\geq 100°$ C., particularly preferably from 120 to 200° C. Very particular preference is given to using solvents selected from the group consisting of monoaryloxyethanols such as phenoxyethanol, monoalkoxyethanol, monosubstituted aromatics, polysubstituted aromatics, decalin, glycerol and water. It is also possible to use mixtures of the abovementioned solvents. Very particular preference is given to using glycerol, phenoxyethanol and/or water.

The ratio of iridium halide or pseudohalide, compound of the formula II and halide scavenger in the process of the present invention is generally 1:4-20:3-6, preferably 1:6-10: 3.1-3.5.

The process of the present invention is generally carried out at from 140 to 230° C., preferably from 180 to 200° C., particularly preferably from 185 to 195° C. The reaction time is generally from 0.1 to 24 hours, preferably from 0.5 to 6 hours, particularly preferably from 0.5 to 2 hours. The process of the present invention thus proceeds significantly more quickly than the processes of the prior art (e.g. DE-A 101 04 426: example 2: 60 hours), so that the process is of interest from an economic point of view and offers a significant advantage over the prior art.

The amount of solvent is generally chosen so that from 0.01 to 2.5 mmol, preferably from 0.2 to 2 mmol, particularly preferably from 0.25 to 0.6 mmol, of iridium halide or pseudohalide is present in 1 ml of solvent.

The desired Ir complex of the formula I is obtained in a yield of generally at least 70%, preferably at least 80%, particularly preferably at least 90%, based on the iridium halide or pseudohalide used, as crude product by means of the process of the present invention. For the purposes of the present invention, a crude product is the product which can be isolated after the reaction without purification operations.

The process of the present invention displays a significantly less pronounced sensitivity of the reaction to the presence of $H_2O$ and $O_2$ than the processes for preparing the corresponding Ir complexes from $Ir(acac)_3$ according to the prior art, i.e. it is possible to use solvents which have been degassed merely by passage of protective gas, preferably for from 1 to 2 hours, or by brief application of a vacuum of at least 0.1 bar with subsequent injection of protective gas rather than complicated degassing of the solvent by freezing.

Owing to the favorable by-product range, highly pure Ir complexes of the formula (I) in phase-pure, preferably crystalline form are obtained by means of simple purification steps. Purification is preferably carried out by sublimation, crystallization, chromatography and/or simple column filtration. The reaction conditions and process steps for the purification are known to those skilled in the art. Column filtration is generally carried out through silica gel using an aprotic nonpolar solvent. Preference is given to using methylene chloride as solvent for column filtration.

Subsequent to the purification, the highly pure Ir complex of the formula (I) obtained is usually dried using methods known to those skilled in the art, e.g. at elevated temperature, at room temperature under reduced pressure or at elevated temperature under reduced pressure.

When using the process of the present invention, the desired high-purity Ir complex of the formula (I) is obtained in a purity of generally >97%, preferably >99.5%, more preferably >99.9%, after a simple purification step as described above.

The high-purity Ir complex of the formula (I) prepared by the process of the invention is preferably present in crystalline form.

Compared to preparative methods starting from $Ir(acac)_3$ customarily used for preparing Ir complexes of the formula (I), the process of the present invention offers the following advantages:

significantly shortened reaction time,
more robust reaction conditions (sensitivity to $O_2/H_2O$, degassing of the solvents used is less intensive),
simple purification by column filtration and
significantly improved product quality without organic contamination.

The significantly improved product quality without organic contamination becomes apparent, in particular, in vaporization of the Ir complexes of the formula (I) prepared in accordance with the present invention. These vaporize completely without leaving a residue, while a black residue of organic material remains when corresponding Ir complexes according to the prior art are vaporized.

Furthermore, the process of the present invention is also suitable for the preparation of large quantities of product, which is important for industrial use of the process.

The Ir complexes of the formula Ia prepared by the process of the present invention are generally predominantly in the form of 2 to 10 μm long and 1 to 3 μm wide platelets, while the corresponding customarily prepared Ir complexes which have phenylpyridyl ligands (from $Ir(acac)_3$) are obtained in the form of 1 to 10 μm long and 0.2 μm wide needles (the values were determined by TEM examination).

The present invention therefore further provides Ir complexes of the formula (I) which are able to be prepared by the process of the invention. Preferred Ir complexes have been mentioned above. The inventive Ir complexes of the formula (I) are highly pure, preferably crystalline and comprise, in particular, no organic impurities. Evaporation of a sample of the inventive Ir complex of the formula (I) therefore leaves no residue.

The process of the invention makes it possible to obtain Ir complexes of the formula (Ia) in phase-pure, preferably crystalline form. For the purposes of the present patent application, "phase-pure, preferably crystalline form" means that a crystal phase which generally comprises from 0 to 5% by weight, preferably from 0 to 2% by weight, particularly preferably from 0 to 0.5% by weight, of a foreign phase is present. Very particular preference is given to a single crystal phase being present, i.e. no (0% by weight) foreign phase is comprised.

In a further embodiment, the present invention provides an Ir complex of the formula (Ia)

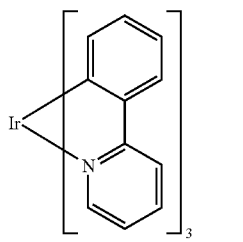

(Ia)

(tris(phenylpyridine)iridium complex; Irppy$_3$), in phase-pure, crystalline form having the following selected Bragg reflections (CuKα) determined by means of powder diffractometry (XRD) using CuKα radiation: 2Θ=10.5, 11.4, 12.9, 15.5, 16.7, 17.0, 18.2, 19.7, 21.0 and 21.5. The measured values of the line positions from which the abovementioned Bragg reflections are determined have a measurement accuracy of +/−0.20°.

Compounds of the formula Irppy$_3$ having structural data according to the present invention are not known from the prior art. The compound of the present invention displays, compared to Irppy$_3$ of the prior art, a significantly improved efficiency when used in OLEDs. If the inventive Ir complex of the formula (Ia) is used as emitter molecule in OLEDs, the efficiency is significantly higher than when using a corresponding compound prepared according to the prior art, as the examples and comparative examples in the present patent application clearly show. An objective comparison of the luminance and efficiency of the compound of the present invention with the data reported in the prior art is difficult, since the efficiency determined is not monocausally dependent on the respective emitter but is also quite sensitive to the precise device architecture, the measurement geometry and the measurement parameters. For this reason, a commercially available compound (H.W. Sands Corp., USA) was compared with the compound of the present invention in an identically constructed device (OLED) in the examples and comparative examples of the present patent application.

In the OLED structure mentioned below, the maximum luminance of the compound of the present invention is 100 000 cd/m² at an emitter layer thickness of 50 nm. The corresponding value for the commercially available material (H.W. Sands Corp., USA) is 80 000 cd/m². The maximum luminance is thus significantly higher (by about 25%) than that of the Irppy$_3$ compounds of the prior art.

Structure of the OLEDs Used:

ITO (indium-tin-oxide)/NPD (layer thickness: about 40 nm)/CBP-Ir(ppy)$_3$ (about 6% by volume) (layer thickness: 10 to 40 nm)/BCP (layer thickness: about 6 nm)/Alq$_3$ (layer thickness: about 20 nm)/LiF (layer thickness: about 2 nm)/Al The efficiency in the OLEDs can be defined by the following parameters:

Luminance L (cd/m²):

This is the quotient of light intensity and luminous area. The luminance can be determined directly by means of a luminance measurement instrument.

Luminous Efficiency η$_{ph}$ (cd/A):

$\eta_{ph}=L/J$

The luminous efficiency is the quotient of the luminance and current density. The internal quantum efficiency can be broken down further into the quantum efficiencies of the underlying physical part processes. A distinction has to be made here between a fluorescent emitter or, for example, a phosphorescent triplet emitter in a host material.

OLEDs comprising the inventive Ir complex of the formula (Ia) as emitter display the following fiirther advantageous properties compared to OLEDs comprising compounds of the prior art (H.W Sands Corp, USA) as emitters:

The luminance at a current density of 10 mA/cm² of OLEDs comprising the compound of the present invention is greater than that of the OLEDs comprising compounds of the prior art. In the case of an OLED having the abovementioned structure, the luminance at a current density of 10 mA/cm² is 2565 cd/m² at an emitter layer thickness of 50 nm. The corresponding value for the material known from the prior art (H.W. Sands Corp., USA) is 2331 cd/m².

The maximum luminous efficiency of OLEDs comprising the compound of the present invention is greater than that of the OLEDs comprising compounds of the prior art. In the case of an OLED having the abovementioned structure, the maximum luminous efficiency is 25-26 cd/A at an emitter layer thickness of 50 nm. The corresponding value for the material prepared according to the prior art (H.W. Sands Corp., USA) is 23-24 cd/A.

The luminous efficiency at a luminance of 100 cd/m² of OLEDs comprising the compound of the present invention is greater than that of OLEDs comprising compounds of the prior art. In the case of an OLED having the abovementioned structure, the luminous efficiency at a luminance of 100 cd/m² is 17.8-18.8 cd/A at an emitter layer thickness of 30 or 40 nm. The corresponding values for the material known from the prior art (H.W. Sands Corp., USA) are 16-15 cd/A.

The inventive Ir complex of the formula (Ia) (Irppy$_3$) thus displays a higher maximum luminance, a higher luminance at a current density of 10 mA/cm², a greater maximum luminous efficiency, a higher luminous efficiency at a luminance of 100 cd/m² and a higher light yield at a luminance of 100 cd/m2 than a corresponding commercially available compound (Irppy$_3$).

Figure 2:
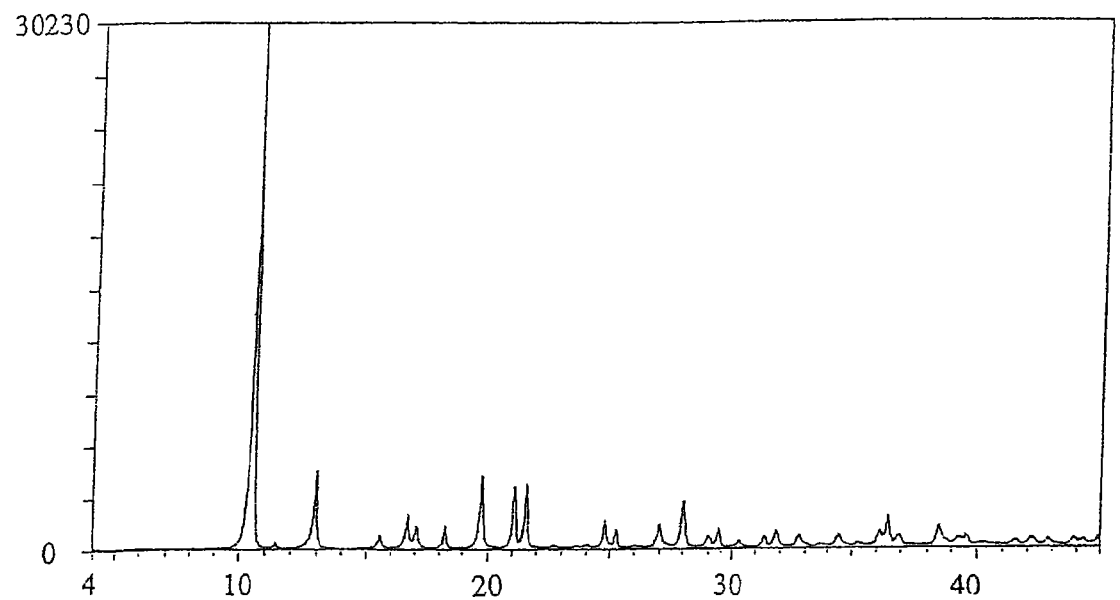
FIG. 2 shows the XRD powder diffraction of Irppy$_3$ prepared by the process of the invention.
Figure 3:
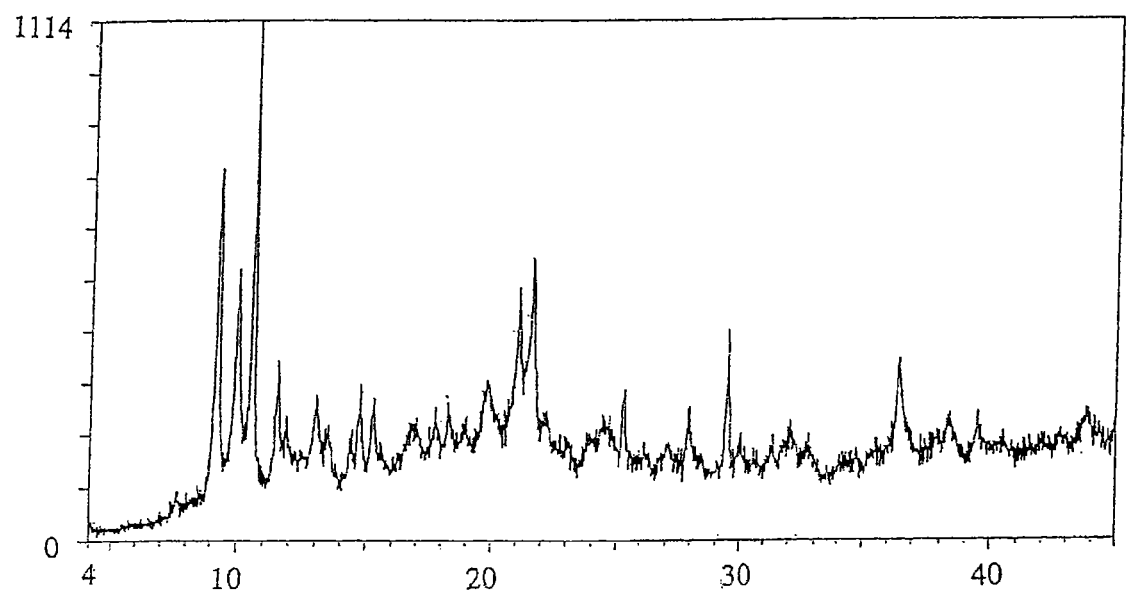
FIG. 3 shows the XRD powder diffraction pattern of commercially available (H.W. Sands Corp., USA) Irppy$_3$.

FIG. 2 shows the XRD powder diffraction pattern of Irppy$_3$ prepared by the process of the invention. In comparison, FIG. 3 shows the XRD powder diffraction pattern of commercially available (H.W. Sands Corp., USA) Irppy$_3$. As can clearly be seen, the Irppy$_3$ prepared by the process of the invention is in phase-pure form, while the commercially available Irppy₃ is in the form of a plurality of phases.

In contrast to the abovementioned data for the compound of the present invention, the Ir(III) complexes of Vladimir V. Grushin et al., Chem. Commun., 2001, 1494-1495 which are prepared in a solvent-free process and have to be purified display a luminous efficiency of only 3.8 cd/A.

In a further embodiment, the present invention provides an Ir complex of the formula (Ib)

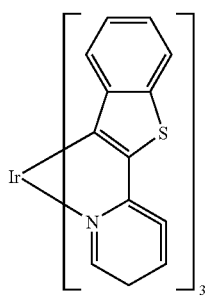

(tris(2-benzo[b]thiophen-2-ylpyridinine)iridium complex, Ir(btp)₃), in crystalline form having the following selected particularly characteristic Bragg reflections (CuK$_\alpha$) determined by means of powder diffractometry (XRD) using CuK$_\alpha$ radiation: 2 θ=9.24, 10.66, 11.91, 14.09, 15.08, 19.21, 20.65, 23.26, 23.87, 24.47. The measured values of the line positions from which the abovementioned Bragg reflections are determined have a measurement accuracy of +/−0.2°.

Ir complexes of the general formula (Ib) which have the structural data according to the present invention are not known from the prior art. The inventive compound of the formula (Ib) has a significantly improved efficiency when used in OLEDs compared to corresponding Ir complexes of the prior art. The inventive Ir complex of the formula (Ib) displays a very good efficiency when used as emitter molecule in OLEDs.

The inventive Ir complexes of the formula (Ia) and (Ib) and also the further Ir complexes of the formula (I) which can be prepared by the process of the invention have, in particular, a high efficiency when used as emitter molecule in OLEDs.

The present invention therefore also provides for the use of an Ir complex of the formula I according to the present invention or prepared by the process of the present invention as emitter molecule in organic light-emitting diodes (OLEDs).

Organic light-emitting diodes (OLEDs) have the basic structure shown in FIG. 1.

In the figure, the reference numerals denote the following:
1 anode
2 hole transport layer
3 light-emitting layer
4 electron transport layer and
5 cathode In the OLEDs, the light-emitting layer is activated by application of an electric potential. The Ir complexes of the formula (Ia) of the present invention are preferably used as emitter molecules in the light-emitting layer (3). However, it is also possible to use the Ir complexes of the present invention in the electron transport layer (4). The present invention therefore also provides a light-emitting layer comprising an Ir complex according to the present invention or an Ir complex prepared by the process of the present invention.

It is possible for further compounds to be present in the light-emitting layer in addition to the Ir complex of the formula (I) of the present invention. For example, it is possible for a fluorescent dye to be present in order to alter the emission color of the Ir complex used as emitter molecule. Furthermore, a diluent material can be used. This diluent material can be a polymer, for example poly(N-vinylcarbazole) or polysilane. However, the diluent material can likewise be a small molecule, for example 4,4'-N,N'-dicarbazolylbiphenyl (CBP) or tertiary aromatic amines. If a diluent material is used, the proportion of the Ir complex of the invention in the light-emitting layer is generally less then 20% by weight, preferably from 3 to 10% by weight.

To obtain particularly efficient OLEDs, the HOMO (highest occupied molecular orbital) of the hole transport layer (2) should be matched to the work function of the anode and the LUMO (lowest unoccupied molecular orbital) of the electron transport layer (4) should be matched to the work function of the cathode.

The present invention further provides an OLED comprising a light-emitting layer according to the present invention.

The further layers in the OLED can be made up of any material which is customarily used in such layers.

The anode (1) is an electrode which provides positive charge carriers. It can, for example, be made up of materials which comprise a metal, a mixture of various metals, a metal alloy, a metal oxide or a mixture of various metal oxides. As an alternative, the anode can be a conductive polymer. Suitable metals include the metals of groups 11, 4, 5 and 6 of the Periodic Table of the Elements and the transition metals of groups 8 to 10. If the anode is to be transparent, it is usual to employ mixed metal oxides of elements of groups 12, 13 and 14 of the Periodic Table of the Elements, for example indium-tin oxide (ITO). It is likewise possible for the anode (1) to comprise an organic material, for example polyaniline, as described, for example, in Nature, Vol. 357, pages 477 to 479 (Jun. 11, 1992). At least the anode or the cathode should be at least partially transparent so that the light produced can be radiated out.

Suitable hole transport materials for the layer (2) of the OLED of the present invention are disclosed, for example, in Kirk-Othmer Encyclopedia of Chemical Technologie, 4th edition, Vol. 18, pages 837 to 860, 1996. Both hole-transporting molecules and polymers can be used as hole transport material. Customarily employed hole-transporting molecules are selected from the group consisting of 4,4'-bis[N-(1-naphthyl)-N-phenylamino]biphenyl (α-NPD), N,N'-diphenyl-N,N'-bis(3-methylphenyl)[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)[1,1'-(3,3'-dimethyl)biphenyl]-4,4'-diamine (ETPD), N,N,N'N'-tetrakis(3-methylphenyl)phenylene-2,5-diamine (PDA), α-phenyl-4-N,N-diphenylaminostryrene (TPS), p-(diethylamino)benzaldehyde diphenylhydrazone (DEH), triphenlamine (TPA) bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), trans-1,2-bis(9H-carbazol-9-yl)cyclobutane (DCZB), N,N,N',N'-tetrakis(4-methylphenyl)(1,1'-biphenyl)-4,4'-diamine (TTB) and porphyrin compounds such as copper phthalocyanines. Customarily employed hole-transporting polymers are selected from the group consisting of polyvinylcarbazoles, (phenylmethyl)polysilanes and polyanilines. It is likewise possible to obtain hole-triansporting polymers by doping polymers such as polystyrene and polycarbonate with hole-transporting molecules. Suitable hole-transporting molecules are the molecules mentioned above.

Suitable electron transport materials for the layer (4) of the OLEDs of the present invention include metals chelated by oxinoid compounds, e.g. tris(8-hydroxyquinolato)aluminum ($Alq_3$), compounds based on phenanthrolines such as 2,9-dimethyl-4,7-diphenyl-1,10-phenanthroline (DDPA) or 4,7-diphenyl-1,10-phenanthroline (DPA) and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). The layer (4) can either serve to aid electron transport or act as a buffer layer or barrier layer to prevent quenching of the exciton at the interfaces of the layers of the OLED. The layer (4) preferably improves the mobility of the electrons and reduces quenching of the exciton.

The cathode (5) is an electrode which serves to introduce electrons or negative charge carriers. The cathode can be any metal or nonmetal which has a work function lower than that of the anode. Suitable materials for the cathode are selected from the group consisting of alkali metals of group 1, for example Li, Cs, alkaline earth metals of group 2 and metals of group 12 of the Periodic Table of the Elements encompassing the rare earth metals and the lanthanides and actinides. It is also possible to use metals such as aluminum, indium, calcium, barium, samarium and magnesium and combinations thereof. Furthermore, lithium-comprising organometallic compounds can be applied between the organic layer and the cathode to reduce the operating voltage.

The OLED of the present invention can further comprise additional layers known to those skilled in the art. For example, a layer which aids the transport of the positive charges and/or matches the band gaps of the layers to one another can be applied between the layer (2) and the light-emitting layer (3). As an alternative, this further layer can serve as a protective layer. In an analogous way, additional layers can be present between the light-emitting layer (3) and the layer (4) in order to aid the transport of the negative charges and/or to match the band gaps of the layers to one another. As an alternative, this layer can serve as protective layer.

In a preferred embodiment, the OLED of the present invention comprises, in addition to the layers (1) to (5), at least one of the further layers mentioned below:

a hole injection layer between the anode (1) and the hole transport layer (2);
a blocking layer for electrons between the hole transport layer (2) and the light-emitting layer (3);
a blocking layer for holes between the light-emitting layer (3) and the electron transport layer (4);
an electron injection layer between the electron transport layer (4) and the cathode (5).

Suitable substances for the individual layers are known to those skilled in the art and are disclosed, for example, in WO 00/70655.

Furthermore, each of the abovementioned layers of the OLED of the present invention can be made up of two or more layers. It is also possible for the surface of some or all of the layers (1), (2), (3), (4) and (5) to have been treated so as to increase the efficiency of charge carrier transport. The choice of materials for each of the layers mentioned is preferably made so as to obtain an OLED having a high efficiency.

The OLED of the present invention can be produced by methods known to those skilled in the art. In general, the OLED is produced by successive vapor deposition of the individual layers on a suitable substrate. Suitable substrates are, for example, glass or polymer films. The vapor deposition can be carried out using customary techniques such as thermal vaporization, chemical vapor deposition and others. In an alternative process, the organic layers can be applied from solutions or dispersions in suitable solvents using coating techniques known to those skilled in the art.

In general, the various layers have the following thicknesses: anode (2): from 500 to 5000 Å, preferably from 1000 to 2000 Å; hole transport layer (3): from 50 to 1000 Å, preferably from 200 to 800 Å; light-emitting layer (4): from 10 to 1000 Å, preferably from 100 to 800 Å; electron transport layer (5): from 50 to 1000 Å, preferably from 200 to 800 Å; cathode (6): from 200 to 10 000 Å; preferably from 300 to 5000 Å. The position of the recombination zone for holes and electrons in the OLED of the present invention and thus the emission spectrum of the OLED can be influenced by the relative thickness of each layer. This means that the thickness of the electron transport layer should preferably be chosen so that the electron-hole recombination zone is located in the light-emitting layer. The ratio of the thicknesses of the individual layers in the OLED is dependent on the materials used. The thicknesses of additional layers used, if appropriate, are known to those skilled in the art.

Use of the inventive Ir complex of the formula (I) as emitter molecule in the light-emitting layer of the OLEDs of the present invention makes it possible to obtain OLEDs having a high efficiency. The efficiency of the OLEDs of the present invention can also be improved by optimizing the other layers. For example, highly efficient cathodes such as Ca, Ba or LiF can be used. Shaped substrates and new hole transport materials which reduce the operating voltage or increase the quantum efficiency can likewise be used in the OLEDs of the present invention. Furthermore, additional layers can be present in the OLEDs in order to adjust the energy level of the various layers and to aid electroluminescence.

The OLEDs of the present invention can be used in all apparatuses in which electro-luminescence is useful. Suitable apparatuses are preferably selected from among stationary and mobile VDUs. Stationary VDUs are, for example, VDUs of computers, televisions, VDUs in printers, kitchen appliances and advertising signs, lighting and information displays. Mobile VDUs are, for example, VDUs in mobile telephones, laptops, vehicles and destination displays on buses and trains.

It is also conceivable for the inventive Ir complexes of the formula (I) to be used in applications other than the OLEDs of the present invention. Examples of such other applications are the use of the inventive Ir complexes of the formula (I) as oxygen-sensitive indicators, as phosphorescent indicators in bioassays and as catalysts.

Furthermore, the inventive Ir complexes of the formula (I) can be used in OLEDs having an inverse structure. In these inverse OLEDs, Ir complexes of the formula (I) are preferably used in the light-emitting layer. The structure of inverse OLEDs and the materials customarily used therein are known to those skilled in the art.

The following examples illustrate the invention.

1. Preparation of Irppy$_3$ 1.1 Preparation of Irppy$_3$ (K. Dedeian et al. *Inorg. Chem.* 1991, 30, 1685-1687) (Comparative Experiment, "acac Route")

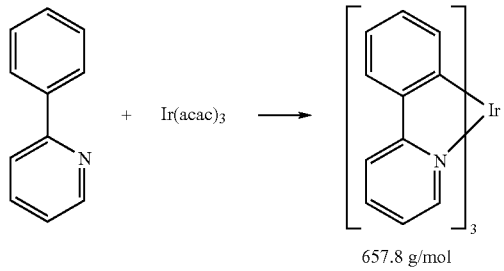

657.8 g/mol

Starting Materials:

| | | |
|---|---|---|
| Ir(acac)$_3$ | 2.50 g | 5.10 mmol |
| 2-phenylpyridine, distilled | 3.17 g | 20.4 mmol |
| Glycerol | 100 ml | |

Procedure:

3.17 g of phenylpyridine together with 100 ml of frozen-out glycerol were placed in a four-neck flask provided with reflux condenser and two-way stopcock and the mixture was degassed by passing argon through it for one hour. At 80° C., Ir(acac)$_3$ was added to the mixture in a countercurrent of argon. The yellow suspension obtained was heated to 200° C. and maintained at this temperature for 18 hours. After cooling, the suspension was filtered through a 75 ml G4 frit. The reaction flask was rinsed out with mother liquor. The residue was washed with a total of 200 ml of deionized water added a little at a time. It was subsequently washed with a total of 45 ml of methanol added in small portions. After removing the washing liquid by means of suction, the residue was dried.

The 2.20 g of crude product obtained were stirred in 130 g of dichloromethane at room temperature for 1 hour. The suspension was filtered through a 125 ml G4 frit. On washing the filter cake, it dissolved in dichloromethane. The solution was passed through a 11 G3 frit which was filled with about 670 ml of silica gel moistened with dichloromethane.

Yield:

After repeated chromatography or HPLC, 800 mg of pure Irppy$_3$ were obtained (23.8%).

Analysis $^1$H-NMR (CD$_2$Cl$_2$, 400 MHz): δ=6.74 (ddd, 1H, $^3$J=7.6 Hz, $^4$J=1.7 Hz, $^5$J=0.6 Hz, 1-H), 6.79 (td, 1H, $^3$J=6.8 Hz, $^4$J=1.4 Hz, 2-H), 6.88 (ddd, 1H, $^3$J=7.7 Hz, $^3$J=6.8 Hz, $^4$J=1.7 Hz, 3-H), 6.92 (ddd, 1H, $^3$J=7.4 Hz, $^3$J=5.5 Hz, $^4$J=1.3 Hz, 7-H), 7.57 (ddd, 1H, $^3$J=5.5 Hz, $^4$J=1.7 Hz, $^5$J=0.9 Hz, 8-H), 7.65 (ddd, 1H, $^3$J=8.2 Hz, $^3$J=7.3 Hz, $^4$J=1.6 Hz, 6-H), 7.67 (ddd, 1H, $^3$J=7.7 Hz, $^4$J=1.5 Hz, $^5$J=0.6 Hz, 4-H), 7.92 (dt, 1H, $^3$J=8.3 Hz, $^4$J=1.0 Hz, 5-H).

1.2 Preparation of Irppy$_3$ Via the Silver Salt Method (According to the Present Invention. "Ag Route")

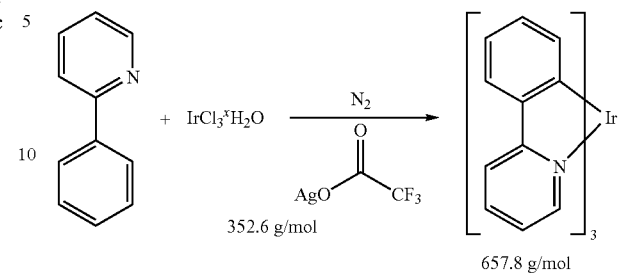

352.6 g/mol    657.8 g/mol

Starting Materials:

| | | |
|---|---|---|
| IrCl$_3$•3 H$_2$O | 2.56 g | 7.26 mmol |
| 2-phenylpyridine, distilled | 10.0 g | 64.5 mmol |
| AgOTf | 5.05 g | 22.4 mmol |
| Glycerol (anhydrous) | 30 ml | |

Procedure:

The reaction apparatus, comprising four-neck flask, reflux condenser, gas inlet tube, two-way stopcock and magnetic stirrer, was flushed with nitrogen for 30 minutes. After the flask had been charged with glycerol and 2-phenylpyridine, a heterogeneous mixture was obtained and this was purged with nitrogen at 80° C. for 1 hour. Iridium chloride trihydrate (dark green powder) was introduced in a countercurrent of nitrogen. This was followed by addition of AgOTf.

On heating slowly to 185° C. (set temperature on the regulator) a brown suspension was obtained at 100° C. After two hours at 185° C, the heating was switched off and the reaction mixture was allowed to cool while stirring under N$_2$.

Work-Up

The mixture was filtered with suction through a 75 ml G3 frit and the residue was washed with 200 ml of water and then with 100 ml of methanol. The residue was then stirred in 370 ml of methylene chloride at room temperature for half an hour and purified by column filtration.

The voluminous light-yellow product obtained was dried overnight at 55° C. in a vacuum drying oven.

Yield:

3.50 g (73%) of the desired product were obtained.

Analysis:

$^1$H-NMR (CD$_2$Cl$_2$, 400 MHz): δ=6.74 (ddd, 1H, $^3$J=7.6 Hz, $^4$J=1.7 Hz, $^5$J=0.6 Hz, 1-H), 6.79 (td, 1H, $^3$J=6.8 Hz, $^4$J=1.4 Hz, 2-H), 6.88 (ddd, 1H, $^3$J=7.7 Hz, $^3$J=6.8 Hz, $^4$J=1.7 Hz, 3-H), 6.92 (ddd, 1H, $^3$J=7.4 Hz, $^3$J=5.5 Hz, $^4$J=1.3 Hz, 7-H), 7.57 (ddd, 1H, $^3$J=5.5 Hz, $^4$J=1.7 Hz, $^5$J=0.9 Hz, 8-H), 7.65 (ddd, 1H, $^3$J=8.2 Hz, $^3$J=7.3 Hz, $^4$J=1.6 Hz, 6-H), 7.67 (ddd, 1H, $^3$J=7.7 Hz, $^4$J=1.5 Hz, $^5$J=0.6 Hz, 4-H), 7.92 (dt, 1H, $^3$J=8.3 Hz, $^4$J=1.0 Hz, 5-H).

The product obtained was examined by means of X-ray powder diffractometry. The structure of the compound was able to be determined on the basis of the powder diffraction pattern. Irppy$_3$ is obtained in phase-pure, crystalline form having the following selected Bragg reflections determined by means of powder diffractometry (XRD): 2Θ=10.5, 11.4, 12.9, 15.5, 16.7, 17.0, 18.2, 19.7, 21.0 and 21.5.

FIG. 2 shows the X-ray powder diffraction pattern ($CuK_\alpha$) of the Irppy$_3$ of the present invention. The angles (2-theta scale) are shown on the abscissa and the intensity (counts) is shown on the ordinate.

FIG. 3 shows the X-ray npwder diffraction pattern ($CuK_\alpha$) of commercially available Irppy$_3$ (H.W. Sands Corp., USA). The angles (2-theta scale) are shown on the abscissa and the intensity (counts) is shown on the ordinate.

Comparison of the X-ray powder diffraction patterns shows that the Irppy$_3$ of the present invention is present in phase-pure form, while the commercially available Irppy$_3$ is present in the form of a plurality of phases. Furthermore, the good signal-to-noise ratio in FIG. 2 compared to the poor signal-to-noise ratio in FIG. 3 shows that the Irppy$_3$ of the present invention is present in significantly higher purity than the commercially available Irppy$_3$.

2. Preparation of Ir(btp)$_3$ 2.1 Preparation of Ir(btp)$_3$ using Iridium Acetylacetonate (Comparative Experiment, "acac Route")

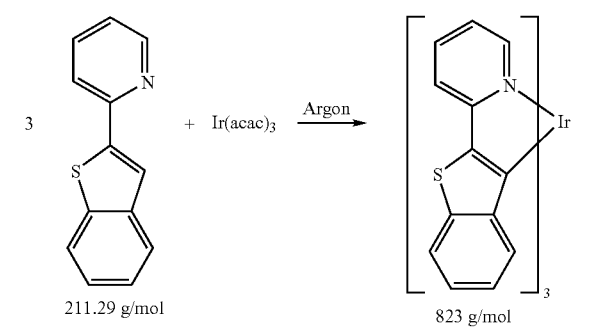

Batch:

| | | |
|---|---|---|
| Iridium acetylacetonate | 0.60 g | 1.22 mmol |
| 2-benzo[b]thiophen-2-ylpyridine | 1.03 g | 4.87 mmol |
| Glycerol | 50 ml | |

Procedure

Argon was passed for one and a half hours into the glycerol which had been degassed in a high vacuum and was being stirred at 60° C. The iridium acetylacetonate and 2-benzo[b]thiophen-2-ylpyridine were introduced in the countercurrent of argon. The reaction mixture was protected from light and stirred under an argon atmosphere (rubber bulb) under reflux (185° C.) for 18 hours. The mixture was filtered at 80° C. The black crystalline product which had deposited on the magnetic stirrer bar was scraped off and added to the residue on the frit. The residue on the frit was very heterogeneous. Yellow, white and dark brown particles could be seen. The residue mixture displayed only very weak red luminescence under UV light. The clear yellow mother liquor did not luminesce under UV light and was discarded. The residue was washed with deionized water and subsequently with methanol. The yellow methanol filtrate did not luminesce under UV light and was discarded. The residue was subsequently washed with 100 ml dichloromethane.

The washed dark brown residue (no luminescence under UV light) was discarded. The dichloromethane filtrate luminesced orange-red under UV light and was evaporated.

Weight of product: 0.24 g/yield: 24% of theory

TLC (thin layer chromatography): product is contaminated ($R_f$=0.93 on silica gel, eluent: $CH_2Cl_2$)

2.2 Preparation of Ir(btp)$_3$ by the Silver Salt Method (According to the Invention, "Ag Route")

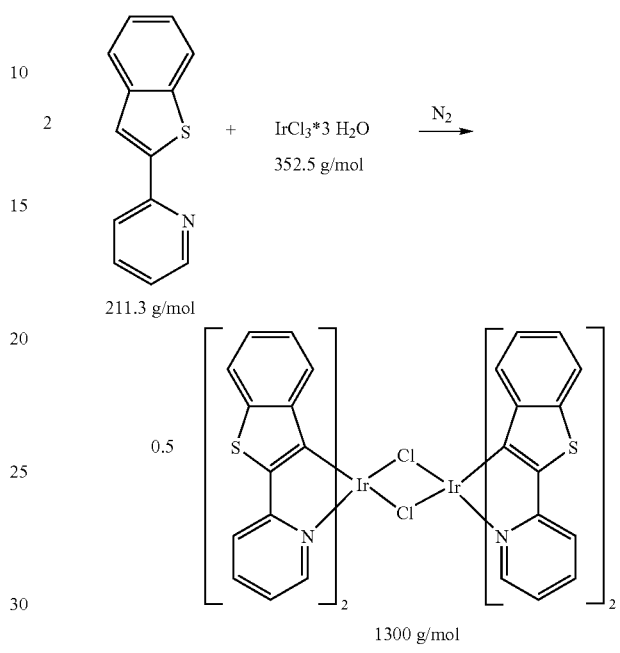

Batch:

| | | |
|---|---|---|
| Iridium trichloride trihydrate | 0.93 g | 2.65 mmol |
| 2-benzo[b]thiophen-2-ylpyridine | 5.00 g | 23.7 mmol |
| Silver trifluoroacetate | 1.85 g | 8.20 mmol |
| Glycerol | 35 ml | |

Procedure:

Nitrogen was passed for 2 hours into the glycerol which was being stirred at 100° C. The 2-benzo[b]thiophen-2-ylpyridine was introduced in the countercurrent of nitrogen. The iridium trichloride trihydrate was introduced into the white suspension, likewise in the countercurrent of nitrogen.

After three minutes, an orange, virtually complete solution which did not luminesce under UV light had been obtained. The introduction of the silver salt resulted in the mixture becoming significantly darker. The flask was shielded from light and was heated to the reflux temperature (185° C.) of the reaction mixture. At the end of the reaction time of two hours, a reddish brown suspension which did not luminesce under UV light had been obtained. The mixture was cooled to 100° C. while stirring. The yellow mixture, in which reddish brown solid had deposited on the magnetic stirrer bar, was separated off at this temperature via a 50 ml G4 frit. The product still present in the flask and that present on the magnetic stirrer bar were combined, crushed in a mortar and slurried in methanol. The reddish brown methanol suspension was filtered through the same frit and the residue was washed with methanol until the washings were clear and colorless. The reddish brown residue was sucked dry and stirred in dichloromethane and the resulting suspension was separated by means of a 50 ml G4 frit.

TLC of the red mother liquor on a silica gel plate using the eluent dichloromethane: product ($R_f$=0.98) is contaminated with ligand ($R_f$=0.68).

The dichloromethane solution was therefore evaporated to about 25 ml and the red crystals which had crystallized out were separated off on a suction filter funnel. The crystals were washed with about 10 ml of methanol into the red mother liquor. The methanol filtrate was clear and colorless at the end. The crystals were thoroughly sucked dry.

Weight of product: 1.67 g/yield: 79% of theory.

$R_f$=0.93 (silica gel, $CH_2Cl_2$)

$^1$H-NMR ($CDCl_3$, 400 MHz): δ=6.58 (d, 1H, J=8.3 Hz), 6.66 (dt, 1H, J=7.2 Hz, J=1.1 Hz), 6.78 (t, 1H, J=5.5 Hz), 7.08 (t, 1H, J=8.1 Hz), 7.37 (d, 1H, J=5.0 Hz), 7.52-7.61 (m, 2H), 7.76 (d, 1H, J=7.0 Hz)

3. Preparation of Ir(piq)$_3$

3.1 Preparation of Ir(piq)3 Using Iridium Acetylacetonate (Comparative Experiment, "acac Route")

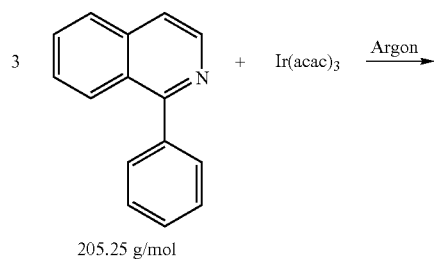

205.25 g/mol

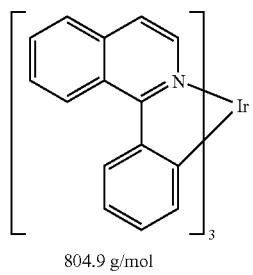

804.9 g/mol

Batch:

| Iridium acetylacetonate | 0.60 g | 1.22 mmol |
|---|---|---|
| 1-phenylisoquinoline | 1.00 g | 4.87 mmol |
| Glycerol | 50 ml | |

Procedure:

Argon was passed for one and a half hours into the glycerol which had been degassed in a high vacuum and was being stirred at 60° C. The iridium acetylacetonate and 1-phenylisoquinoline were introduced in the countercurrent of argon. The reaction mixture was shielded from light and stirred under an argon atmosphere (rubber bulb) under reflux (185° C.) for 21 hours. The initially orange solution had become a dark orange suspension at the end of the reaction time. The suspension was filtered through a frit at about 100° C. and the residue was washed with deionized water.

Weight of product: none. The dark brown residue and its dichloromethane solution and also the mother liquor which had been extracted with dichloromethane displayed, in contrast to the synthesis using iridium trichloride trihydrate and a silver salt, no luminescence! The experiment was not worked up.

3.2 Preparation of Ir(piq)$_3$ by the Silver Salt Method (According to the Invention, "Ag Route")

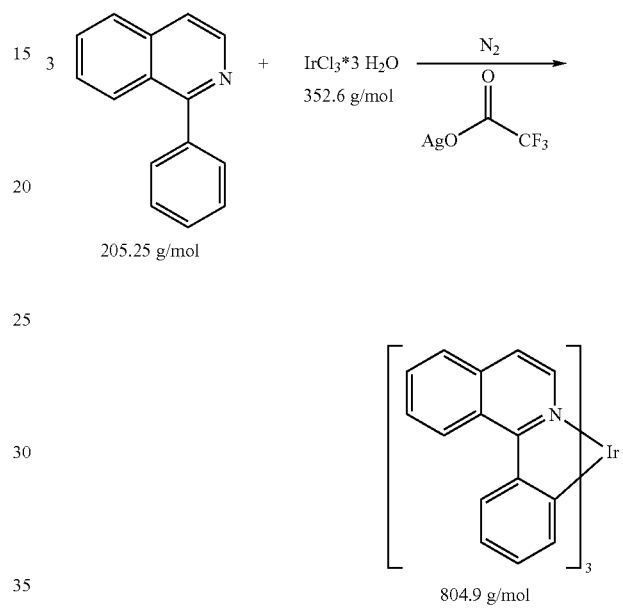

Batch:

| Iridium trichloride trihydrate | 0.97 g | 2.75 mmol |
|---|---|---|
| 1-phenylisoquinoline | 5.03 g | 24.5 mmol |
| Silver trifluoroacetate | 1.92 g | 8.50 mmol |
| Glycerol | 40 ml | |

Procedure:

Nitrogen was passed for one and a half hours into the glycerol which was being stirred at 100° C. The 1-phenylisoquinoline was introduced in the countercurrent of nitrogen. The iridium trichloride trihydrate and the silver trifluoroacetate were introduced into the clear and colorless solution, likewise in the countercurrent of nitrogen. The reaction mixture was shielded from light and stirred under a nitrogen atmosphere (rubber bulb) under reflux (185° C.) for 2 hours. The suspension was filtered through a frit at about 100° C. and the residue was washed with 160 ml of a mixture of methanol and deionized water (1:1) and subsequently stirred in hot dichloromethane and filtered through a frit. The dichloromethane mother liquor was evaporated.

Weight of product: 1.68 g/yield: 76.4% of theory.

Mass (EI): 804.0, 805.0, 806.0 (M$^+$)

4. Summary of the Results from the Metallation Examples 1 to 3

TABLE 1

| Ligand | Phenylpyridine | | 2-benzo[b]-thiophen-2-ylpyridine | | Phenylisoquinoline | |
|---|---|---|---|---|---|---|
| Starting materials | Ir(acac)$_3$ | IrCl$_3$•H$_2$O Ag(OTf) | Ir(acac)$_3$ | IrCl$_3$•H$_2$O Ag(OTf) | Ir(acac)$_3$ | IrCl$_3$•H$_2$O AgOTf |
| Reaction temperature | 200° C. | 185° C. | 185° C. | 185° C. | 185° C. | 185° C. |
| Reaction time | 18 h | 2 h | 18 h | 2 h | 21 h | 2 h |
| Batch size | 5.10 mmol | 7.26 mmol | 4.87 mmol | 23.7 mmol | 4.87 mmol | 24.5 mmol |
| Yield | 23.8% | 73% | 24% | 79% | n.d. | 76.4% |

The results in Table 1 above show that the process of the invention ("Ag route") is significantly superior to the process of the prior art ("acac route") in the following respects:
- reaction time
- simplicity of purification
- yield.

5. Physical Results on the Ir Complexes Ir(btp)$_3$ and Ir(biq)$_3$ from Examples 2.2 and 3.2

The absorption and emission spectra of the Ir complexes Ir(btp)$_3$ and Ir(biq)$_3$ were measured at a concentration of 2 mg/l in toluene. The luminescence quantum yields were determined at a concentration of about 2 mg/l in toluene solutions saturated with air. The results are summarized in Table 2 below.

Table 2 reports, firstly, the abovementioned physical properties in toluene (i.e. in solution) and. secondly, the abovementioned properties in bulk (i.e. in powder form).

Figure 4:
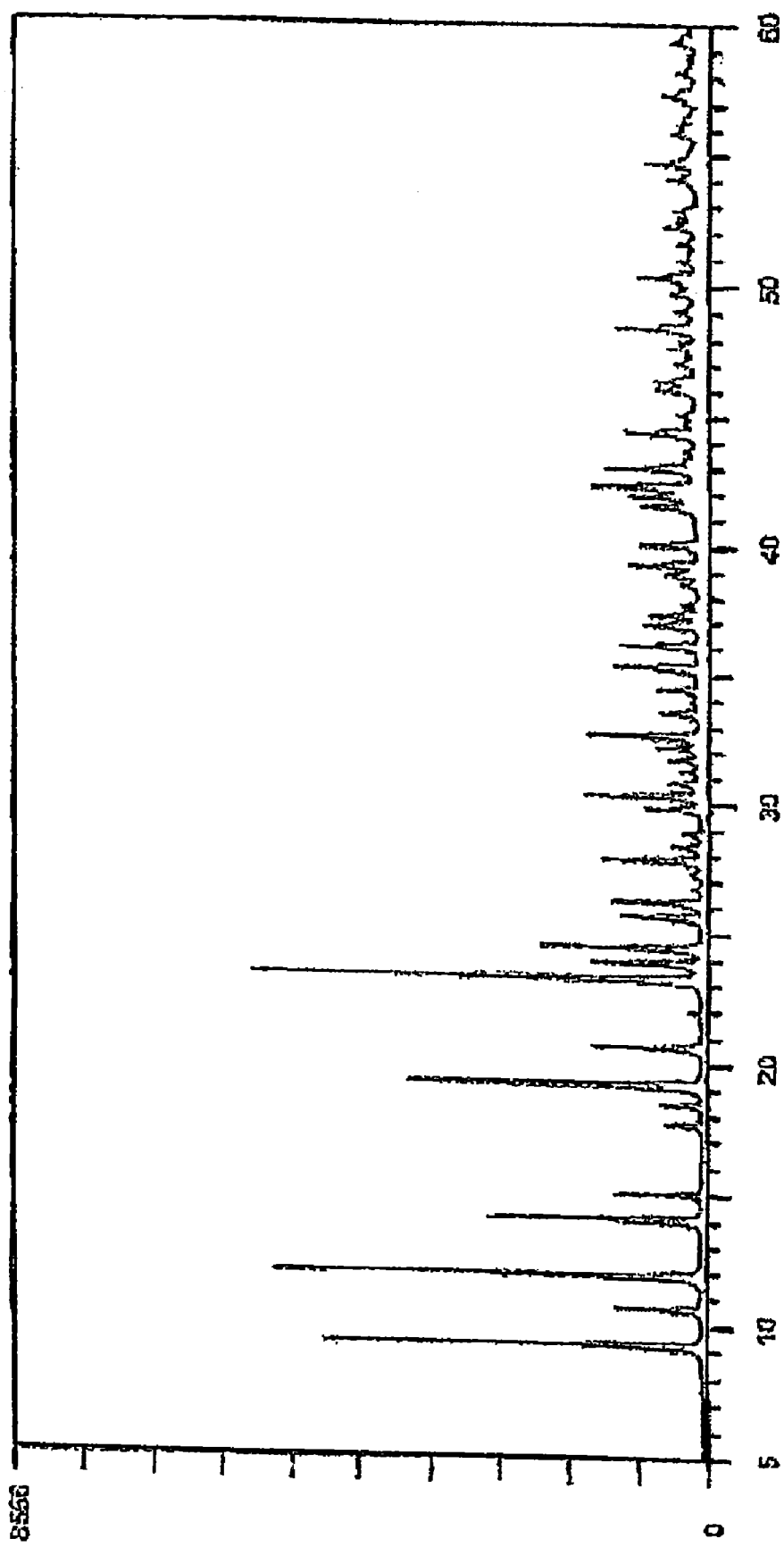
FIG. 4 shows the X-ray powder diffraction pattern (CuK$_α$) of the Ir(btp)$_3$ according to the invention.

FIG. 4 shows the X-ray powder diffraction pattern (CuK$_\alpha$) of the Ir(btp)$_3$ according to the invention. The angles (2-theta scale) are shown on the abscissa and the intensity (counts) is shown on the ordinate.

6. Use of Irppy$_3$ in OLEDs

Commercially available Irppy$_3$ (H.W. Sands Corp., USA) and the Irppy$_3$ prepared according to the present invention (example 1.2; "Ag route") were each tested in an OLED having the following structure:

TABLE 2

Overview of the spectroscopic data on the cyclometallated compounds obtained

| Ir complex | Solv. | $\lambda_{abs}$ max nm | $\lambda_{em}$ max nm | QY % | CIE 1931 x | CIE 1931 y | | $\lambda_{em}$ of $\lambda_{max}$ powder nm | CIE 1931 x | CIE 1931 y |
|---|---|---|---|---|---|---|---|---|---|---|
| Ir(biq)$_3$ | Toluene | 431 | 618 | 1.3 | 0.53 | 0.26 | Powder | 667 | 0.65 | 0.33 |
| Ir(btp)$_3$ | Toluene | 408 | 597 | 0.2 | 0.55 | 0.36 | Powder | 614/645 | 0.63 | 0.33 |

In Table 2, the abbreviations have the following meanings:

| | |
|---|---|
| Solv. | solvent |
| $\lambda_{abs}$ max | wavelength of maximum absorption |
| $\lambda_{em}$ max | wavelength of maximum emission |
| QY | quantum yield (the quantum yield was determined by a method based on the methods disclosed in J. W. Eastman, J. Photochem. Photobiol., 6, 55-72, 1967; J. N. Demas, G. A. Crossby, J. Phys. Chem. 75, 991-1025, 1971 (Review) and D. F. Eaton, J. Photochem. Photobiol., 2, 523-531, 1988) |
| CIE 1931 | Commission Internationale de L'Eclairage, chromaticity coordinates |

The quantum yield QY is the internal quantum yield and is defined as the ratio of the number of photons emitted to the total number of photons absorbed.

| | |
|---|---|
| anode: | ITO (indium-tin oxide) |
| hole transport layer: | α-NPD (4,4'-bis[N-(1-naphthyl)-N-phenylamino]-biphenyl) (thickness: about 40 nm) |
| light-emitting layer: | CBP (4,4'-N,N'-dicarbazolylbiphenyl) comprising 6% by volume of Irppy$_3$ (thickness: about 20-50 nm) |
| blocking layer for holes: | BCP (2,9-dimethyl-4,7-diphenyl-1,10-phenanthroline) (thickness: about 6 nm) |
| electron transport layer: | Alq$_3$ (tris(8-hydroxyquinolinato)aluminum) (thickness: about 20 nm) |
| electron injection layer: | LiF (thickness: about 2 nm) |
| cathode: | Al |

The performances of OLEDS using Irppy$_3$ according to the present invention ("Ag route") and using commercially available Irppy$_3$ from H.W. Sands Corp., USA ("Sands") are compared in the following Table 3.

TABLE 3

Performances of OLEDs using Irppy₃

| Compound | Thickness [nm] | Max. luminance [cd/m²] | Luminous efficiency at 100 cd/m² [cd/A] | Luminance at 10 mA/cm² | Max. luminous efficiency [cd/A] |
|---|---|---|---|---|---|
| "Ag route" | 30 | 67350 | 17.8 | 1956 | 20.1 |
| (ex. 1.2) | 40 | 88370 | 18.8 | 2330 | 23.3 |
| | 50 | 102100 | 18.0 | 2565 | 25.7 |
| "Sands" | 30 | 52580 | 16.0 | 1762 | 18.1 |
| | 40 | 67680 | 15.1 | 2237 | 22.4 |
| | 50 | 79340 | 18.5 | 2331 | 23.7 |

The terms used in the columns of the table have the following meanings:

| | |
|---|---|
| Compound: | Irppy₃ used or process by which the Irppy₃ used has been prepared ("Sands": comparative experiment, ex. 1.2: example 1.2 according to the present invention) |
| Thickness: | Thickness of the emitter layer in nm |
| Max. luminance: | Maximum luminance in cd/m² at the voltage indicated in the next column to the right |
| Luminous efficiency at 100 cd/m² | Luminous efficiency in cd/A at a luminance of 100 cd/m² and the voltage indicated in the next column to the right |
| Max. luminous efficiency | Maximum luminous efficiency in cd/A at the voltage indicated in the next column to the right |

It can be seen from the table that
for emitter layers having thicknesses of 30, 40 and 50 nm, higher maximum luminances are achieved when using the Irppy₃ according to the present invention (example 1.2)
for emitter layers having thicknesses of 30 and 40 nm, higher luminous efficiencies at a luminance of 100 cd/m² are achieved when using the Irppy₃ according to the present invention (example 1.2)
for emitter layers having thicknesses of 30, 40 and 50 nm, higher luminances at a current density of 10 mA/cm² are achieved when using the Irppy₃ according to the present invention (example 1.2)
for emitter layers having thicknesses of 30, 40 and 50 nm, higher maximum luminous efficiencies are achieved when using the Irppy₃ according to the present invention (example 1.2).

We claim:
1. A process for preparing a compound of the formula (I)

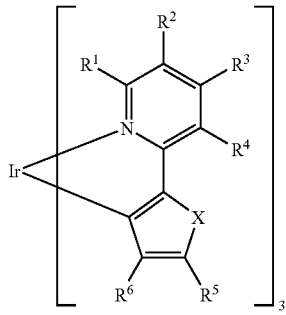

(I)

wherein
X is $-CR^7=CR^8-$, $-S-$, $-NR^9-$, $-O-$, $-Se-$,
$R^1$, $R^2$, $R^3$, $R^4$, $R^5$, $R^6$, $R^7$ and $R^8$
are independently H, straight chain or branched $C_{1-20}$-alkyl, cyclic $C_{3-20}$-alkyl, wherein one or more adjacent $CH_2$-groups of the alkyl groups may be replaced by $-O-$, $-S-$, $-NR^{10}-$, or $-CONR^{11}-$, and one or more H-atoms of the alkyl groups may be replaced by F, Cl, Br or CN; aryl or heteroaryl with a skeletal structure having 4 to 14 C-atoms, wherein one or more C-atoms may be replaced by heteroatoms selected from $-O-$, $-S-$, $-N-$ and $-P-$, and the C-atoms and optionally the heteroatoms may be substituted with non aromatic substituents, as defined for $R^1$ to $R^8$; F, Cl, Br or CN; or
two adjacent groups $R^1$, $R^2$, $R^3$, $R^4$, $R^5$, $R^6$, $R^7$ and $R^8$ together form a cyclic group, which may be again substituted with the groups mentioned concerning $R^1$, $R^2$, $R^3$, $R^4$, $R^5$, $R^6$, $R^7$ and $R^8$, wherein two adjacent substituents of the cyclic group may form again a cyclic group;
$R^9$, $R^{10}$, $R^{11}$
are independently H, straight chain or branched $C_{1-20}$-alkyl, cyclic $C_{3-20}$-alkyl, which may be substituted as defined concerning the groups $R^1$ to $R^8$ or aryl or heteroaryl as defined concerning $R^1$ to $R^8$;
by reacting a ligand of formula (II)

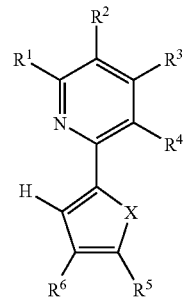

(II)

wherein the symbols $R^1$, $R^2$, $R^3$, $R^4$, $R^5$, $R^6$ and X having the meaning mentioned above,
with an iridium halide or pseudohalide of the formula $IrZ_3$ or $IrZ_3 \cdot L_x$, where Z is a halide or pseudohalide and L is an organic or inorganic molecule, and x is the number of L and is 1 to 3;
in the presence of a halide scavenger selected from the group consisting of Ag-, Hg-, Sb- and Al-salts, wherein the process is carried out in a solvent and the amount of solvent is chosen so that from 0.01 to 2.5 mmol of iridium halide or pseudohalide is present in 1 ml of solvent.

2. The process as claimed in claim 1, wherein
X is —CH=CH— or —S—.

3. The process as claimed in claim 2, wherein
X is —CH=CH— and
$R^1$, $R^2$, $R^3$, $R^4$, $R^5$, $R^6$ each are H, or
X is CH=CH— and $R^1$, $R^2$, $R^5$, and $R^6$ each are H and $R^3$ and $R^4$ form together a 6-membered aromatic group, which is unsubstituted, or
X is —S— and $R^1$, $R^2$, $R^3$, $R^4$ each are H and $R^5$, $R^6$ form together a 6-membered aromatic group, which is unsubstituted.

4. The process as claimed in claim 1, wherein the ratio of iridium halide or pseudohalide, ligand of formula II and halide scavenger is 1:4 to 20:3 to 6.

5. The process as claimed in claim 1 which is carried out at a temperature from 140 to 230° C.

6. The process as claimed in claim 1, wherein the compound of the formula (I) obtained is purified by sublimation, crystallization, chromatography or simple column filtration.

7. A compound of formula (I)

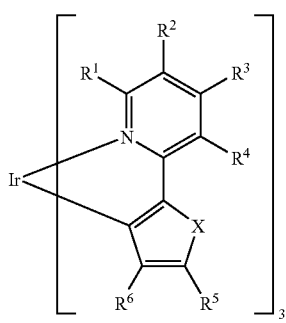

(I)

wherein
X is —$CR^7$=$CR^8$—, —S—, —NR—, —O—, —Se—,
$R^1$, $R^2$, $R^3$, $R^4$, $R^5$, $R^6$, $R^7$ and $R^8$
are independently H, straight chain or branched $C_{1-20}$-alkyl, cyclic $C_{3-20}$-alkyl, wherein one or more adjacent $CH_2$-groups of the alkyl groups may be replaced by —O—, —S—, —$NR^{10}$—, or —$CONR^{11}$—, and one or move H-atoms of the alkyl groups may be replaced by F, Cl, Br or CN; aryl or heteroaryl with a skeletal structure having 4 to 14 C-atoms, wherein one or more C-atoms may be replaced by heteroatoms selected from —O—, —S—, —N—and —P—, and the C-atoms and optionally the heteroatoms may be substituted with non aromatic substituents, as defined for $R^1$ to $R^8$; F, Cl, Br or CN; or
two adjacent groups $R^1$, $R^2$, $R^3$, $R^4$, $R^5$, $R^6$, $R^7$ and $R^8$ together form a cyclic group, which may be again substituted with the groups mentioned concerning $R^1$, $R^2$, $R^3$, $R^4$, $R^5$, $R^6$, $R^7$ and $R^8$, wherein two adjacent substituents of the cyclic group may form again a cyclic group;

$R^9$, $R^{10}$, $R^{11}$
are independently H, straight chain or branched $C_{1-20}$-alkyl, cyclic $C_{3-20}$-alkyl, which may be substituted as defined concerning the groups $R^1$ to $R^8$ or aryl or heteroaryl as defined concerning $R^1$ to $R^8$;
obtained by a process as claimed in claim 1.

8. The compound as claimed in claim 7
wherein
X is —CH=CH— and $R^1$, $R^2$, $R^3$, $R^4$, $R^5$, $R^6$ each are H, or
X is CH=CH— and
$R^1$, $R^2$, $R^5$, and $R^6$ each are H and
$R^3$ and $R^4$ form together a 6-membered aromatic group, which is unsubstituted, or
X is —S— and $R^1$, $R^2$, $R^3$, $R^4$ each are H and
$R^5$, $R^6$ form together a 6-membered aromatic group, which is unsubstituted.

9. A compound of the formula (Ia)

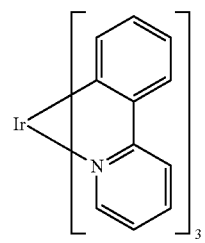

(Ia)

in phase-pure, crystalline form having the following selected Bragg reflections determined by means of powder diffractometry (XRD) with $CuK_\alpha$-radiation; 2θ=10.5, 11.4, 12.9, 15.5, 16.7, 17.0, 18.2, 19.7, 21.0 and 21.5.

10. A compound of the formula (Ib)

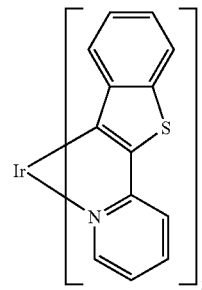

(Ib)

in crystalline form having the following selected Bragg reflections determined by means of powder diffractometry (XRD) with $CuK_\alpha$-radiation: 2θ=9.24, 10.66, 11.91, 14.09, 15.08, 19.21, 20.65, 23.26, 23.87, 24.47.

* * * * *